United States Patent [19]

Bender

[11] 4,206,407
[45] Jun. 3, 1980

[54] CONTINUITY TESTER FOR CONTAINER LININGS

[75] Inventor: William J. Bender, West Long Branch, N.J.

[73] Assignee: American Can Company, Greenwich, Conn.

[21] Appl. No.: 938,083

[22] Filed: Aug. 30, 1978

[51] Int. Cl.² ........................................... G01N 27/42
[52] U.S. Cl. .................................... 324/446; 324/449
[58] Field of Search ...................... 324/29, 30 R, 30 B, 324/54, 65; 204/1 T

[56] References Cited

U.S. PATENT DOCUMENTS

| 3,555,414 | 1/1971 | Deichelmann | 324/54 |
|---|---|---|---|
| 3,719,884 | 3/1973 | Laroche | 324/54 |
| 3,858,114 | 12/1974 | Voellmin | 324/29 |
| 3,863,146 | 1/1975 | Ehret | 324/29 |
| 3,965,415 | 6/1976 | Ehret | 324/54 |

*Primary Examiner*—Michael J. Tokar
*Attorney, Agent, or Firm*—Robert P. Auber; Stuart S. Bowie; William C. Hosford

[57] ABSTRACT

An improved apparatus for evaluating the continuity of the enamel lining of metallic containers. The apparatus has been developed for quality control inspection of containers and is designed to ensure that the entire interior surface of the container is evaluated by the test. The apparatus utilizes cooperating carbon electrodes of opposite polarity, an electrolyte solution, a grounded container, an enabling circuit and a meter to measure current flow through defects or discontinuities in the enamel lining. The carbon electrodes include a primary or measuring electrode, and a short secondary or liquid sensing electrode.

Electrolyte solution is added until contact is established between the primary and the sensing electrodes thereby activating an enabling circuit which is used to control the meter display. By positioning the sensing electrode at the upper boundary of the enamel lining proximate the mouth of the container, the user is assured that the container has been sufficiently filled with electrolyte to permit proper evaluation of the container.

4 Claims, 3 Drawing Figures

CONTINUITY TESTER FOR CONTAINER LININGS

BACKGROUND OF THE INVENTION

The can making industry is characterized by a line of products which are produced in very high volume, with high quality control standards, but where the profit contribution of each unit is small. As a consequence there is a need for quality control methods which are rapid, effective and which require little judgement on the part of the operator, who may be unskilled. One of the factors which is routinely evaluated is the continuity of the enamel lining of the container. Since the enamel lining serves to protect the product from possible contamination by interaction with the metal and at the same time protects the can from deterioration, the enamel must be free from voids or defects. It is well known that discontinuities in a coating can be detected by impressing a low voltage across the coating in the presence of an electrolyte and observing whether a flow of current occurs. The electrolyte fills the voids or coating discontinuities and establishes a conductive path between the grounded metallic substrate upon which the coating is deposited and the electrode in contact with the electrolyte. Kronstein et al describe such a method in Industrial and Engineering Chemistry Volume 42, Pages 1568-72 (1950). Kronstein used paper saturated with dilute potassium nitrate as the electrolyte. The substrate was made the anode in the circuit and metallic ions were captured on the paper and subsequently precipitated to form a colored salt, thereby indicating current flow and the presence of a void.

Pipe and tank linings have been evaluated for continuity using a sponge saturated with a dilute salt solution, which is mounted on a wand. The wand is connected to one terminal of a DC power supply and the tank or pipe is connected to the other terminal. Discontinuities in the coating are located by a bell in the circuit which rings when current flow occurs.

More recently, the technique has been used in the container industry. An instrument known as the WACO Enamel Rater manufactured by the Wilkens-Anderson Company rates the lined container by measuring the current flow in milliamperes. The test requires that the container be filled to within ⅛" of the top of the can, that the electrode be lowered into the can and the test be allowed to proceed for the stipulated period, after which a measurement is made. In most instruments, the meter is of the analog type wherein the deflection of a needle is observed and a reading is estimated from the scale. In some cases a digital meter is available, but even this is subject to misinterpretation since a dead meter or a broken circuit gives a reading which is equivalent to that of a good continuously lined container. Since a properly filled container is apt to result in spillage due to the proximity of the fluid level to the top of the container, there is a definite tendency on the part of an inspector to under fill the cans. This is particularly true in a production line environment where there is pressure to keep up with the production. Where the can is under filled by even a fraction of an inch, the continuity test is unsatisfactory since the area of the container adjacent to the rim is critical, and will not be included in an under filled can. Currently available instruments fail to distinguish between a properly and improperly filled container.

Accordingly, it is an object of this invention to provide an improved continuity tester for container linings which ensures that the entire interior surface of the lined container is evaluated for continuity during a test.

It is also an object of this invention to provide an improved continuity tester which is easy to read, does not require interpolation or estimation of the output and where an open circuit, cannot be misinterpreted for a satisfactory response.

Finally, it is an object of this invention to provide an instrument which is compatible with an industrial environment, which is rugged, reliable and may be handled by a relatively unskilled operator.

The inventor is not aware of any patents which are material to the examination of the application.

SUMMARY OF THE INVENTION

It may be seen that the aforementioned objects of the invention may be attained in an apparatus for evaluating the continuity of a container lining, which provides for connecting the container body to a D.C. power supply, filling the container with an electrolyte solution, and subsequently subjecting the lined container to a D.C. potential by means of a primary electrode inserted into the electrolyte solution. The primary electrode and the container body are connected to opposite terminals of the power supply. The apparatus further includes a meter introduced between the power supply and the primary electrode to measure current flow through defects in the container lining, between the primary electrode and the container body. In addition, the apparatus incorporates as an improvement over prior art a means for sensing electrolyte fluid which is disposed at the mouth of the container body proximate the primary electrode. The sensing means which extends into the container body a predetermined distance, is responsive to contact with the electrolyte solution, emitting a signal when contact is effected. An enabling circuit is incorporated in the apparatus, which receives the signal emitted by the sensing means modifies it, stores it and transmits it to a meter thereby activating the meter display means. More particularly the apparatus incorporates as an improvement, a sensing electrode. The sensing electrode carries the same polarity as the container body. It is disposed at the mouth of the container body proximate the primary electrode and extends into the mouth of the container sufficiently to permit the tip of the sensing electrode to contact the surface of a predetermined level of electrolyte placed therein. Thus the sensing electrode is connected to the negative terminal of the power supply through the electrolyte solution and the primary electrode 28. The apparatus further incorporates an enabling circuit which comprises an amplifier, a timing means and a memory element. The amplifier receives the signal from the sensing electrode, amplifies the signal and transmits it to the memory element and to the timing means. The apparatus further includes a digital display element for the meter, which is normally blank but is activated by a signal received from the sensing electrode through the enabling circuit thereby enabling the meter to measure and display current flow through discontinuities in the container lining from the primary electrode to the can body.

It is preferable that the apparatus incorporates a protective plastic sheath around the primary electrode and the sensing electrode. Each of the plastic sheaths are counter bored to provide a chamber adjacent to the electrode surface. The chambers are provided with vent holes for the dissipation of air or gases. The plastic sheaths protect the electrodes from physical abuse and additionally prevent the ready short circuiting thereof.

Finally, it is preferable that the apparatus be wired so that the container body and the sensing electrode are connected to the positive (+) terminal of the D.C. power supply and that the primary electrode is connected to the negative (−) terminal of the D.C. power supply.

DETAILED DESCRIPTION OF THE ILLUSTRATED EMBODIMENT

Figure 1:
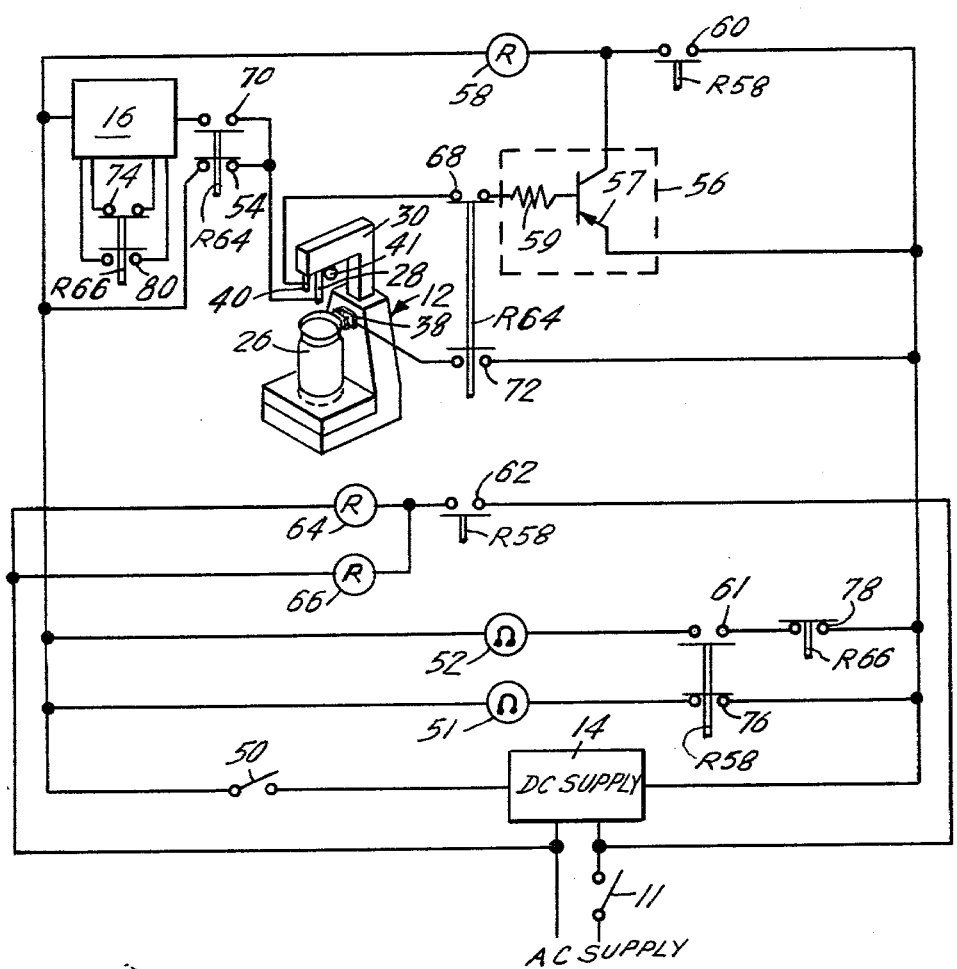
FIG. 1 is a circuit diagram of the continuity tester embodying the present invention.
Figure 2:
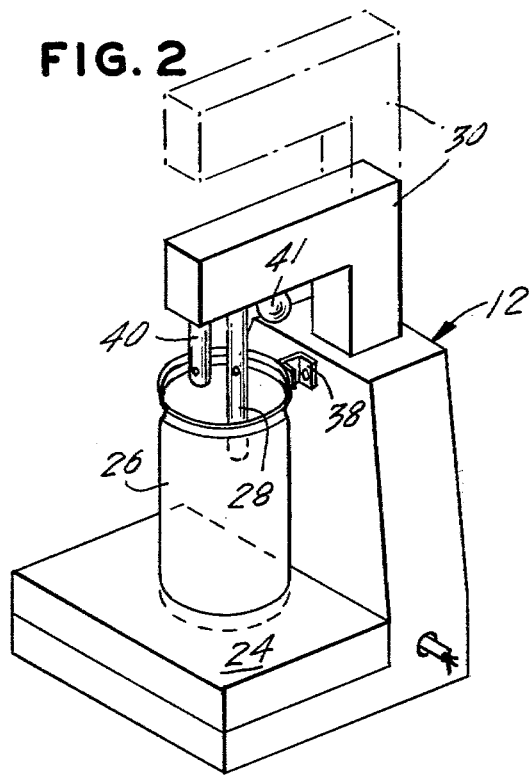
FIG. 2 is a perspective view of the test stand of the continuity tester showing the electrode arm in the operating position with the elevated attitude of the arm indicated in phantom. The figure additionally includes a container positioned for evaluation.
Figure 3:
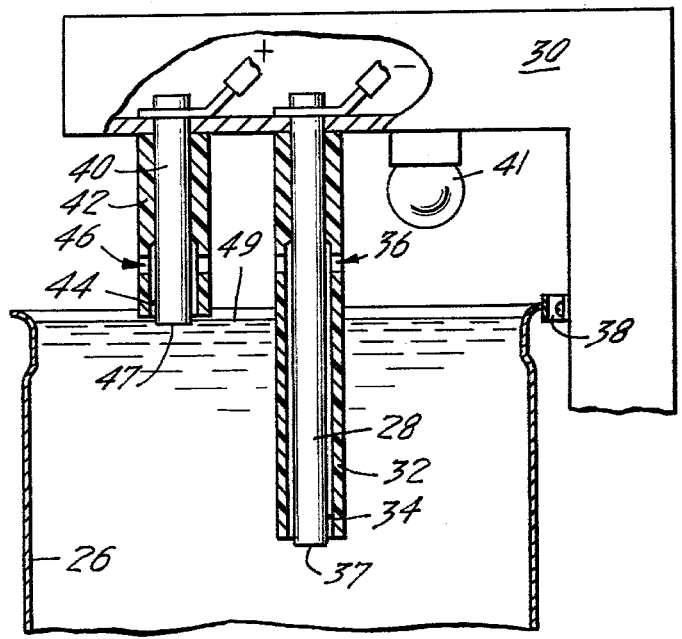
FIG. 3 is a cross sectional view through the electrode arm of the test stand of FIG. 2, showing the primary electrode, the sensing electrode. The container is indicated.

Turning now in detail to FIG. 1 of the appended drawings, therein illustrated is a circuit diagram of the improved continuity tester for container linings consisting of a test stand 12, a power supply 14, a meter 16 and an enabling circuit. The test stand 12, best seen in FIG. 2, has a base 24 contoured to securely receive a lined container 26 for evaluation. A spring contact 38 which is affixed to test stand 12 makes firm contact with the rim of the container body 26 when the container is received within the base. A primary electrode 28 is suspended from an arm 30 which is mounted in test stand 12 for vertical movement. The arm 30 may be elevated and retained in place, as shown in phantom, for loading and unloading of container bodies. The arm may then be lowered to operating position, as illustrated, thereby closing a microswitch (not shown) located in the base of the stand which turns on an inspection lamp 41 which provides focused light for the visual examination of the lining of container 26. The microswitch also serves to activate or reset the apparatus. In the operating position, primary electrode 28 is axially aligned with container body 26 extending therein a substantial predetermined distance, below the desired maximum level of the contents. The primary electrode which is carbon is sheathed with plastic tubing as best seen in FIG. 3. The tubing is counter bored to provide electrolyte solution chamber 34 surrounding the lower portion of the electrode. The upper region of the counter bored chamber is provided with a series of vent holes 36 to prevent the entrapment of air or gases. The electrode is mounted in arm 30 by conventional means not shown.

A sensing carbon electrode 40 is mounted on arm 30 adjacent to the primary electrode. The sensing electrode 40 is sheathed with plastic tubing 42 counter bored to provide a chamber 44 which chamber terminates with a series of vent holes 46. The plastic sheaths which encircle the electrodes are designed to provide protection against physical abuse and accidental short circuiting. Additionally, the sheaths deter the deliberate thwarting of the level sensing feature. The sensing electrode 40 is appreciably shorter than the primary electrode 28 since the sensing electrode is designed so that the tip 47 thereof will establish contact with the surface 49 of the electrolyte placed in container 26. In contrast, the primary electrode 28 is a measuring electrode and is designed to extend into container 26 so that a substantial portion thereof is in contact with the electrolyte. The primary electrode contact area extends from upper boundary 49 which is in proximate alignment with tip 47 of the sensing electrode to the tip 37 of the primary electrode.

Returning to FIG. 1, current is supplied from an AC source through an ON-OFF switch 11, to power supply 14. Power supply 14 is a regulated 6 V DC power supply Model EAPS6-2.5 supplied by ADTECH. The negative terminal of the power supply is connected to the primary electrode 28 through a normally closed contact 54 operated by a 1 sec 110 volt time delay relay coil 64—supplied by Potter Brumfield Model No. RIS-30A-IIS-X4EI. A parallel path is provided through meter 16 and normally open contact 70 also operated by relay 64. Meter 16 is a Weston 2470 series meter with a digital display having 200 milliamp full scale read out with a 4½" digit 100 microamp resolution. While other meters may be employed, it is considered preferable that the display be capable of being blanked until a signal is received from the enabling circuit causing the display to be illuminated. A meter which shows a reading particularly a reading of zero when the meter is inoperative is not satisfactory since the inspector cannot readily determine whether the zero reading indicates a properly lined container or an open circuit both of which would indicate a reading of zero current flow. The positive terminal of the power supply 14 is connected to spring clip 38 on test stand 12 passing thru normally open contact 72. Contact 72 is operated by time delay relay 64. The positive terminal is also connected through amplifier 56 and normally closed contact 68 to the sensing electrode 40. Amplifier 56 consists of a Sylvania ECG129 transitor connected to a 1000 ohm resistor. A parallel path is provided through normally open contact 60, which serves as a memory element and which is operated by relay coil 58 Model MPC 4C supplied by Gould.

An indicating light 51 controlled by normally closed contact 76 which is operated by relay 58 calls for electrolyte addition. A second indicating light 52 is controlled by a pair of contacts in series. The first contact 78 is a normally closed contact operated by 5 second time delay relay 66 which relay coil is powered by 100 V AC and is supplied by Potter Brumfield Model No. R15-30A-115- X4EI. The second contact 61 for indicating light 52 is a normally open contact operated by relay 58.

In operation, switch 11 is turned to the ON position activating the power supply. Arm 30 of the test stand 12 is raised out of the way to the upper position where a friction means, not shown, engages the vertical portion thereof to hold the arm in the load-unload position. A lined can body which is to be evaluated is then placed on the test stand 12 within the recess in base 24 provided therefore. Spring contact 38 bears against the uncoated can rim to provide an electrical connection therewith. Arm 30 is then lowered to the operating position. When the arm has been fully lowered, limit switch 50 is automatically closed thereby lighting inspection light 41 and indicating lamp 51, which is energized by current flowing through normally closed contact 76. Current flows from limit switch 50 through normally closed contact 54 to center electrode 28. The indicating lamp calls for electrolyte addition and will remain on until sufficient electrolyte has been added to provide a conductive path between electrode 28 and electrode 40. The current flows from electrode 40 through normally closed contact 68 to the base of transitor 57 thereby energizing the transitor and subsequently the coil of relay 58. At this point, contact 76 opens, thereby causing lamp 51 to go out signifying that sufficient electrolyte has been added to container 26. Contact 60 is closed by relay 58 and will continue to hold in, thereby keeping relay 58 energized even after the initiating signal from transitor 57 is no longer present. Contact 62 which is also closed by relay 58 will then energize time delay relays 64 and 66. Concurrent therewith contact 61 which is also closed by relay 58 energizes lamp 52 indicating that the timing sequence has been initiated. After a 1 second interval normally closed contacts 54 and 68 are opened and normally open contacts 70 and 72 are closed. This sequence serves to remove the sensing electrode from the current path and direct current flow from the negative terminal of the power supply 14 through meter 16 through contact 70, through electrode 28 through the electrolyte solution, through defects or discontinuities in the container lining, through can body 26 through contact 72 to the positive terminal of the power supply. After a 5 second delay, contact 74 opens thereby unblanking the display at the same time contact 80 is closed to hold the final meter reading for the test period. Concurrent therewith contact 78 is opened thereby turning off lamp 52.

What is claimed is:

1. An apparatus for evaluating the continuity of a container lining of the type wherein said lined container body is connected to one terminal of a D.C. power supply and is filled with an electrolyte solution and subsequently subjected to a D.C. potential by means of a primary electrode which is connected to the opposite terminal of said D.C. power supply and which is immersed in said electrolyte to form an electrolyte cell and wherein a meter is introduced between said power supply and said primary electrode to measure defects by sensing current flow between said container and said primary electrode, the improvement comprising:
   (a) sensing means, disposed at the mouth of said container body proximate said primary electrode, extending into said container body a predetermined distance, responsive to contact with said electrolyte solution, said sensing means emitting a signal when solution contact is effected;
   (b) an enabling circuit for receiving said signal from said sensing means and for modifying, storing and transmitting said signal; and
   (c) display means for said meter activated by said signal received from said sensing means through said enabling circuit thereby enabling said display means to display current flow, through coating discontinuities from said primary electrode to said container body, measured by said meter.

2. An apparatus for evaluating the continuity of a container lining of the type wherein said lined container body is connected to one terminal of a D.C. power supply and is filled with an electrolyte solution and subsequently subjected to a D.C. potential by means of a primary electrode which is connected to the opposite terminal of said D.C. power supply and which is immersed in said electrolyte to form an electrolyte cell and wherein a meter is introduced between said power supply and said primary electrode to measure defects by sensing current flow between said container and said primary electrode the improvement comprising:
   (a) a sensing electrode carrying the same polarity as said container body disposed at the mouth of said container body proximate said primary electrode, wherein said sensing electrode enters the mouth of said container body sufficiently to permit the tip thereof to establish contact with the surface of a predetermined level of said electrolyte solution placed therein;
   (b) an enabling circuit comprising:
      (i) an amplifying means for receiving and amplifying the signal from said sensing electrode;
      (ii) timing means responsive to a signal received from said amplifying means;
      (iii) a memory element for storing said amplified signal; and
   (c) a digital display element for said meter which is normally blank but is activated by a signal received from said sensing electrode through said enabling circuit thereby enabling said meter to measure and display current flow through coating discontinuities from the primary electrode to said container body.

3. An apparatus as defined in claim 2 wherein said primary electrode and said sensing electrode are each protected in a plastic sheath where said plastic sheaths are counter bored to provide a fluid area adjacent said electrode surface and where vent holes are provided to permit the dissipation of air or gases, whereby said plastic sheaths protect said electrodes from mechanical abuse and additionally prevent the short circuiting of said electrodes.

4. The apparatus as defined in claim 2 wherein said container and said sensing electrode are connected to the positive (+) terminal of the D.C. power supply and where said primary electrode is connected to the negative (−) terminal of the D.C. power supply.

* * * * *